United States Patent [19]

Schnell et al.

[11] Patent Number: 4,723,956

[45] Date of Patent: Feb. 9, 1988

[54] PORT FREE CONTAINER

[75] Inventors: William J. Schnell, Libertyville; James A. Fitzgerald, McHenry, both of Ill.

[73] Assignee: Baxter Travenol Laboratories, Inc., Deerfield, Ill.

[21] Appl. No.: 905,738

[22] Filed: Sep. 10, 1986

Related U.S. Application Data

[63] Continuation of Ser. No. 650,400, Sep. 14, 1984, abandoned.

[51] Int. Cl.[4] ............................................ A61M 25/00

[52] U.S. Cl. .................................... 604/414; 604/262; 604/408

[58] Field of Search ................ 604/262, 408, 414, 415

[56] References Cited

U.S. PATENT DOCUMENTS 2,698,619 11/1955 Beacham et al. .................. 604/408
2,986,142 5/1961 Bieberdorf et al. ................ 604/262
3,030,952 4/1962 Elder .................................. 604/262
3,991,912 11/1976 Soto .................................. 604/262

*Primary Examiner*—C. Fred Rosenbaum
*Assistant Examiner*—Sherri E. Vinyard
*Attorney, Agent, or Firm*—Paul C. Flattery; John P. Kirby; Garrettson Ellis

[57] ABSTRACT

In a container defining a flexible wall, means for sealingly receiving a puncture member through the wall which comprises an insert member positioned within the container. The insert member defines an aperture for sealingly receiving the puncture member after penetration through the wall. The aperture provides flow communication between the container interior and a puncture member received in the aperture. Thus, access may be provided to a container which has no conventional tubular port carried on its exterior. Optionally, tape means may be removably adhered to the flexible wall so that removal of the tape means exposes a clean surface through which the puncture member can penetrate.

23 Claims, 12 Drawing Figures

FIG. 4
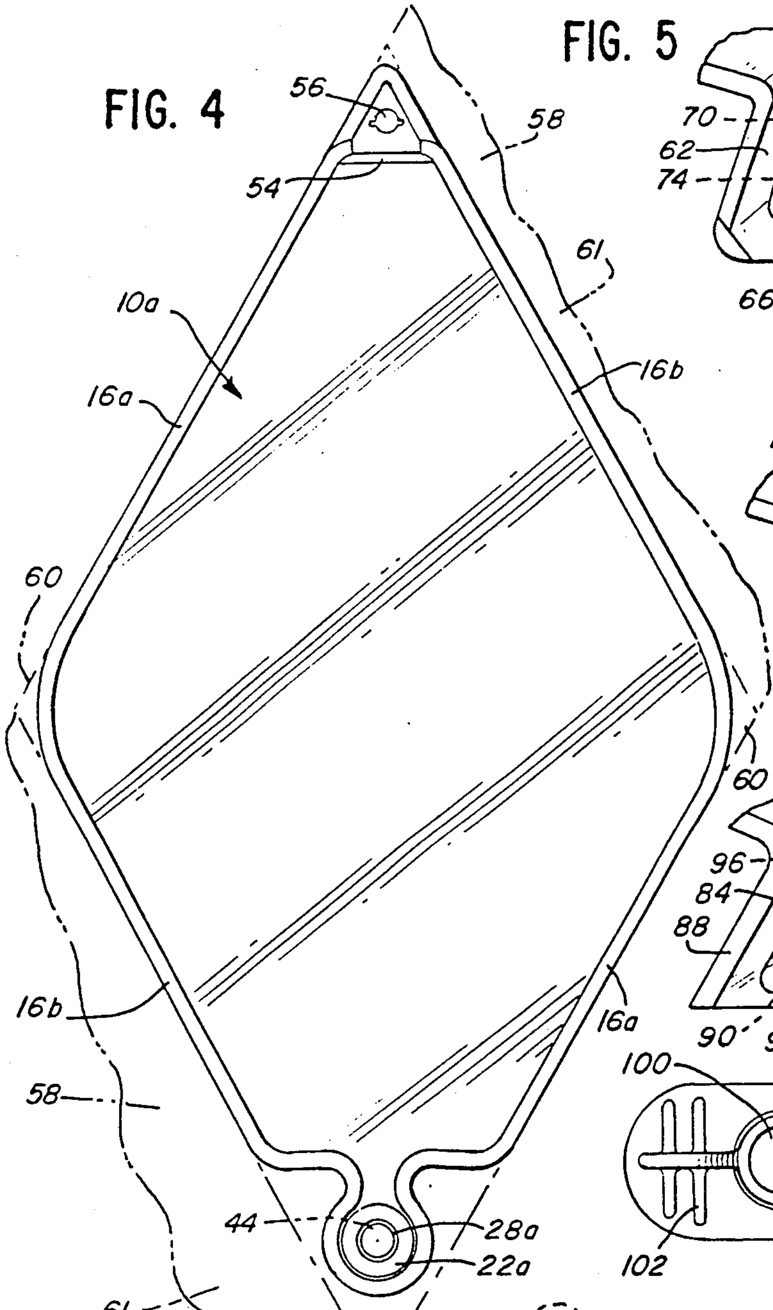
FIG. 5
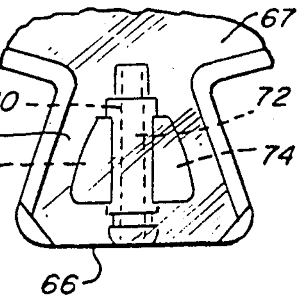
FIG. 6
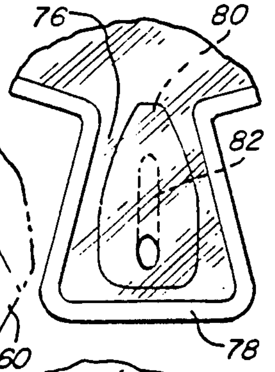
FIG.7
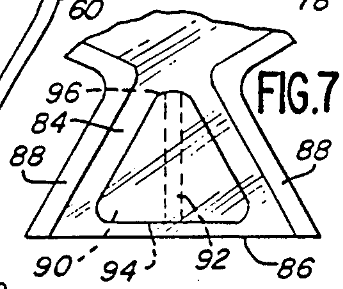
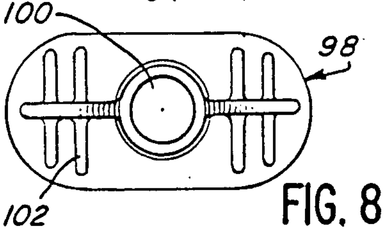
FIG. 8
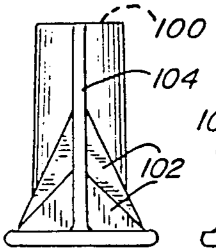
FIG. 9
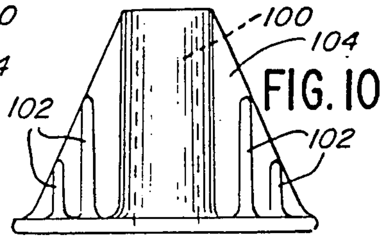
FIG. 10

PORT FREE CONTAINER

This is a continuation of application Serial No. 650,400, filed Sept. 14, 1984 now abandoned.

TECHNICAL FIELD AND PRIOR ART

This application relates to an improved container having flexible plastic walls, for sterile solutions or the like. Flexible plastic solution containers are used in great quantities in the medical field for holding sterile solution for intravenous use, blood, sterile washing solutions, peritoneal dialysis solutions and the like. Typical designs of flexible containers include the Viaflex ® containers for intravenous solutions and the Dianeal ® peritoneal dialysis solution containers sold by Travenol Laboratories, Inc.

Conventional flexible plastic containers carry tubular ports at one end which are proportioned to receive a spike connector of an administration set. The spike connector passes into a tubular port passing through a diaphragm into flow communication with the solution contents of the container.

The medical industry is currently under strong economic pressure to reduce costs. Thus, there is particularly important value to be obtained from container designs which can be manufactured with reduced cost.

One significant facet of the cost of a flexible container is the cost of the access port. In Bieberdorf et al. U.S. Pat. No. 2,949,712, a design of flexible container is proposed which has no tubular access port on the outside of the container, but instead a puncture is made through the container wall itself. Problems, however, result from the fact that the spike which penetrates the container wall is not well supported for use. Thus leakage can develop around the puncture site of the spike, and the spike is susceptible to being accidentally dislodged from its bag-penetrating position.

The Entri-Pak™ container of Biosearch Medical Products, Inc. of Somerville, New Jersey is an aluminum foil-plastic laminated bag of enteral feeding diet material, with a projecting, flexible-walleo protrusion. The protrusion seals a tube which is closed with a membrane. The tube, in turn, passes through the bag wall for communication with the bag interior. The outer end of the protrusion is torn away to expose the outer end of the tube, which may then be spiked with the spike connector of an administration set.

In accordance with this invention, flexible plastic containers are provided which are highly susceptible to inexpensive, automated manufacture, and which may be free of outwardly protruding tubular access ports which must be preformed and sealed to the container during the manufacturing operation. Thus, significant economies of manufacturing can be achieved through the invention of this application.

DESCRIPTION OF THE INVENTION

In this invention, a container is provided defining a flexible wall. Means for sealingly receiving a puncture member through the wall are present, comprising an insert member positioned within the container. The insert member defines an aperture for sealingly receiving the puncture member after penetration through the wall.

The aperture provides flow communication between the container interior and a puncture member received in the aperture. Typically, the aperture is a bore extending through the insert member.

As the puncture member passes into the aperture, it typically causes an annular portion of the container wall to deform or stretch into a position between the puncture member and the aperture wall, where the annular portion can be sealingly locked and seated between the connected puncture member and aperture wall. Thus, leakage can be prevented.

The container wall may define a flexible-walled protrusion communicating with the rest of the container through a relatively narrow neck portion, to permit flow communication between the protrusion and the rest of the container. The insert member is advantageously captured or retained in the protrusion, to provide it with a fixed location without the need to seal it to the inner wall of the container.

The container may also carry removable tape means on the outer surface of the flexible wall. The tape means may be applied to the container prior to sterilization, so that the tape means may be removed, when use of the container is desired, to expose a clean, typically sterile surface for puncturing by the puncture member. Thus, no alcohol swab or the like may be required prior to the use of the device of this invention.

The container of this invention may be made from a pair of plastic sheets, or a large, extruded, flattened tubular plastic sheet, by appropriate peripheral heat sealing in a manner analogous to present commercial container manufacture techniques. Alternatively, a plastic sheet may be folded over and then peripherally sealed together on all open sides to form the container. The insert member may in this circumstance be simply placed between facing plastic sheets within the newly-formed container before the peripheral sealing operation, to provide a very efficient, cost effective manufacturing technique, since no separate application of port tubes is required. Alternatively, blow molding or other techniques may be used to manufacture the container.

While a wide range of thermoplastic or other resilient materials may be used to make the container wall, one preferred material is DYPRO ®Z4650 polypropylene copolymer, sold by the Arco Chemical Company. The plastic material used may, if desired, be about 0.01 inch thick and may optionally be a coextrusion of the above recited DYPRO plastic material as an inner layer, and polypropylene as an outer layer of the container wall. The insert member, in turn, may be made from a polypropylene material, for example having about 3 weight percent of copolymerized ethylene units in the formulation.

If desired, the insert member may comprise a pair of tubes in telescoping relation with each other and connected at one end, with the aperture as defined above being defined by the bore of the inner tube. This structure provides a certain desirable resilience to the insert member, and facilitates the seal formed between a puncture member and the aperture wall.

In the specific instance of DYPRO ®Z4650 copolymer, it is be desirable for the insert member to be made of a generally rigid material such as polypropylene as mentioned above. However, in other instances, for use with other resilient sheet materials, it may be desirable to use a softer, semiflexible insert member. The aperture of the insert member may be proportioned to be of a diameter which is dependent upon the wall thickness of the facing plastic sheets, so that on penetration of the container wall by a puncture member, the annular portion of the container wall is formed by deformation and stretching into the desired sealing position between the puncture member and the aperture wall.

The various dimensions and proportions of the system may vary in accordance with frictional characteristics of the puncture member and insert member with the plastic of the container wall to optimize the formation of the desired deformed or stretched annular portion used for sealing between the connected puncture member and aperture wall. Additionally, one may adjust the sharpness of the puncture member to provide the desired results. For example, it may be desired to provide a sharp spike with a highly resilient material, coupled with materials that provide a rather high coefficient of friction. On the other hand, when using a bag wall material that is not very resilient, a duller spike may be desired in some instances, and one may wish to use materials that have a relatively lower coefficient of friction. On the other hand, a sharp spike may be used in this instance as well for facilitating access to the container.

Accordingly, it is believed to be basically a routine matter to select materials for the container wall and insert member, and to proportion them into proper dimensions, to achieve good results with a large number of different materials in accordance with this invention.

DESCRIPTION OF THE DRAWINGS

In the drawings.

FIG. 4 is a plan view of another embodiment of container using the invention of this application.

FIGS. 5 through 7 are fragmentary, plan views of alternate designs of the flexible-walled protrusion of the container of this invention, containing alternate designs for the insert member.

FIG. 8 is a plan view of an alternate design of insert member.

FIGS. 9 and 10 are elevational views, rotated 90° about their longitudinal axis from each other, of the insert member of FIG. 8.

DESCRIPTION OF SPECIFIC EMBODIMENTS

Figure 1:
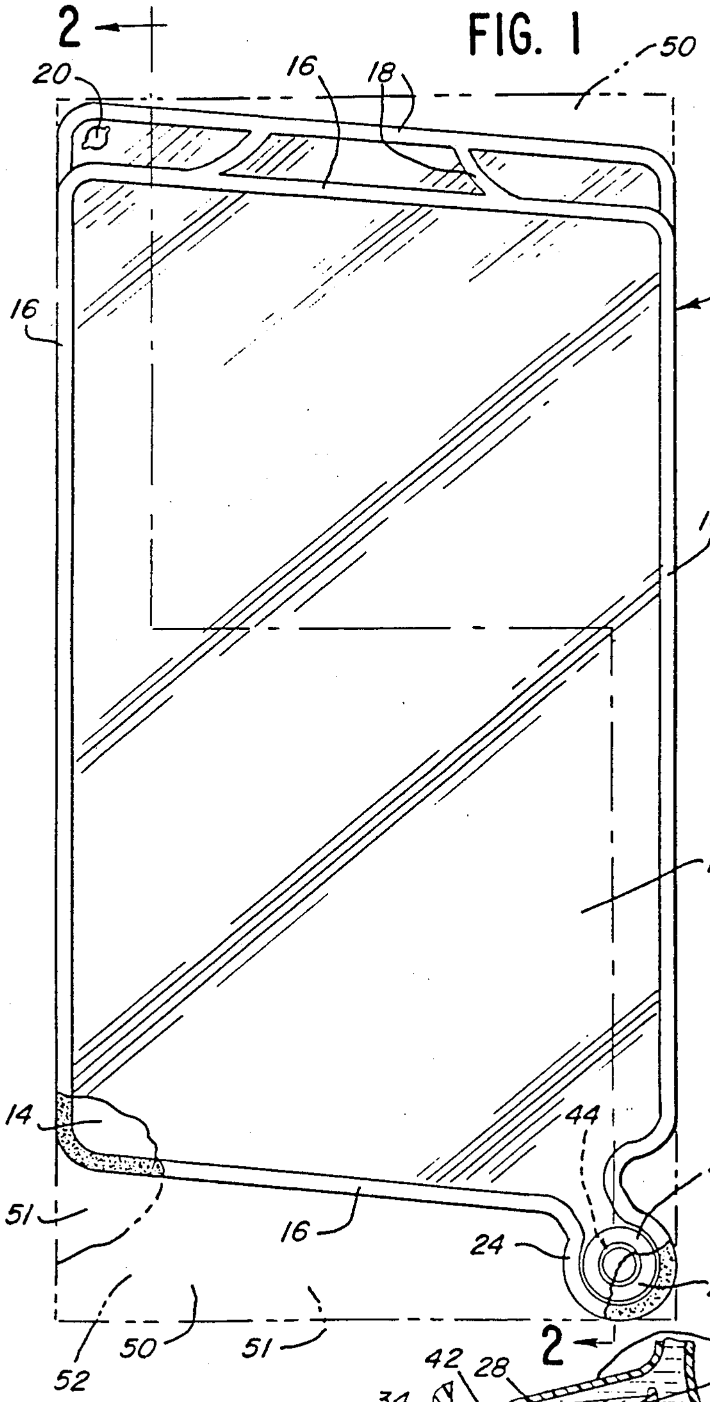
FIG. 1 is a plan view of a flexible, collapsible container, with a portion broken away, utilizing the invention on this application.
Figure 2:
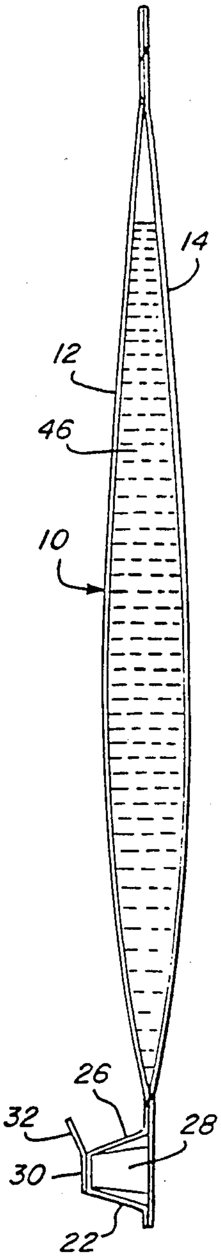
FIG. 2 is a side elevational view of the container of FIG. 1, taken along line 2—2 of FIG. 1.
Figure 3:
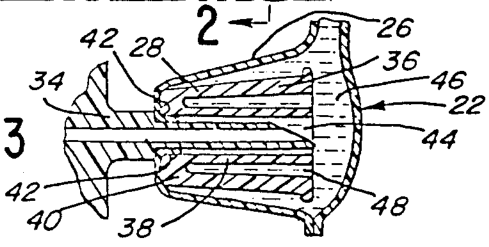
FIG. 3 is a fragmentary, longitudinal sectional view of a portion of the container of FIGS. 1 and 2, showing how a spike may penetrate the bag wall and the insert member to provide access to the contents of the container.

Referring to FIGS. 1 through 3, one embodiment of the invention of this application is disclosed. Container or bag 10 is made of a pair of overlying thermoplastic sheets 12, 14, which are heat sealed together. A peripheral heat seal 16 is used. The seal may be made by conventional radio frequency sealing processes if polyvinylchloride sheeting is used, or by a hot bar seal if polyolefin sheeting or the like is used.

The top of container 10 may carry other peripheral seals 18, and a corner hanger hole 20 for suspension of the container. At the other end of container 10 from hanger hole 20, and at the opposed corner thereof, flexible-walled protrusion 22 is defined, being surrounded by the extension 24 of heat seal 16.

As shown in FIG. 2, for example, sheet 12 defines a portion of protrusion 22 which may be thermoformed in conventional manner to form a pocket 26. Pocket 26, in turn, receives and holds insert member 28, which may be a molded plastic piece of a design shown in longitudinal section in FIG. 3.

As another desired feature, tape member 30 may be provided, adhering to an outer end of pocket 26 as shown in FIG. 2. Tape member 30 may be a known plastic foil tab which is sealed to bag 10, defining a handle portion 32, so it can be manually removed to expose the surface of pocket 26 underneath foil tab 30. If foil tab 30 is applied and then bag 10 is radiation or steam sterilized, for example, removal of tab 30 can present a sterile surface to the user for application of a spike connector 34 to bag 10 to obtain access thereto.

As shown in FIG. 3, insert member 28 may be a single, molded plastic piece comprising a pair of tubular portions 36, 38, joined together at one end 40 in telescoping relation. The outer telescoping portion 36 serves as a good manual gripping member, so that one may hold protrusion 26 with the fingers, thus also gripping insert member 28. One then may then manually advance spike 34, penetrating the wall of protrusion 26 to gain access to container 10. Portions of the container wall 42 may be stretched to fold inwardly into bore 44 of insert member 28 as spike 34 penetrates bore 44, so that wall portions 42 provide an added sealing lip or ring to the connection system between spike 34 and insert member 28. Accordingly, liquid 46 in container 10 may pass through the lumen of spike 34 into an administration set or the like, for flow communication between the bag interior and the set to which spike 34 is attached.

The telescoping tube structure of insert member 28 provides a certain resilience to the tube 38 defining bore 44 which can improve the sealing characteristics of the insert member with spike 34. Also, less plastic is used, when compared with a solid piece insert member which does not define annular space 48.

The illustration of FIG. 3 is somewhat schematic. The inner wall of tube 38 defining bore 44 will be commonly expected to contact the outer wall of spike 34, to provide improved sealing along most of its length. The cut and folded-in portions 42 of the bag wall provide extra sealing, typically stretching insert member 28 outwardly a small amount to accommodate for their presence.

While the container of this invention may be made by blow molding or the like, the specific design of FIG. 1 is contemplated to be made on a mass production basis by heat sealing together two overlapping continuous webs 50, 51 of plastic material to form the container walls 12, 14, respectively after inserting insert member 28 between webs 50, 51 in its desired position. The two overlapping, continuous plastic webs 50, 51 shown in phantom lines represent the portion of continuous plastic web material (for example, a roll of material) that typically may be allocated to the manufacture of a single container. It can be seen that high efficiency of use can be obtained, with excess portions of the plastic web material being typically trimmed away by an automatic trimmer as part of the manufacturing process. If desired, an adjacent bag on the production line may be defined in continuous webs 50, 51 with its flexible-walled protrusion 22 facing bag 10 and occupying the area indicated by reference numeral 52, for further economy of manufacturing.

It can be seen that the heat seals 16 at the respective ends of container 10 are formed to be in angular relationship other than 90° to the lateral heat seals 16 of the edges of webs 50, 51. When container 10 hangs on a pin projecting through hole 20, protrusion 22 is the lowest point of container 10, so that all liquid will pass into protrusion 22 and thus out of spike 34. Even if container 10 is held perpendicular to the ground for draining, the slight downward slope of the lower end seal line 16 will assure that all liquid passes into protrusion 22.

Alternatively, protrusion 22 may be placed at a centered location of container 10 at the lower end thereof, and hanger hole 20 may also be centered.

Referring to FIG. 4, another design of container of this invention is disclosed. Container **10*a* once again is made by peripheral heat sealing along seal lines 16*a*, 16*b* to form a generally diamond-shaped container. Flexible walled protrusion 22*a* may be of substantially similar design to protrusion 22, and may contain an insert member 28*a* which may be of similar design to insert member 28. Inner heat seal 54 is provided at the top of the container to separate its contents from hangar hole 56**.

It should be noted that this design provides particular efficiency, in providing a very low scrap rate from a continuous web of overlapping plastic sheets 58 from which container **10*a* may be made. This may be accomplished by providing that peripheral seal lines 16*b* which are nonparallel to the edges 60 of plastic webs 58, are not perpendicular to such edges 60, but define an angle with them of typically 35° to 70°, i.e. an acute angle. It can be seen that a very low scrap rate of web material to be trimmed away from the container is provided by this configuration, since other containers 10*a* can be formed in portions 61 of overlapping web material 58**.

Referring to FIG. 5, another design of flexible protrusion 62 for a container is disclosed. In this case, the two side walls of container 64 may be formed by folding a web along fold line 66 at the end of protrusion 62, and forming peripheral heat seals 68 with insert member 70 inside. Insert member 70 is shown to define bore 72 extending from end to end thereof, and also to define a pair of opposed, lateral projections 74 to facilitate manual gripping of the insert member by the user within flexible-walled protrusion 62.

Referring to FIG. 6, another design of container is shown having flexible-walled protrusion 76, with the container being otherwise of similar and generally conventional design. Protrusion 76 may be defined by a peripheral heat seal line 78 which passes across its end, but such heat seal line does not interfere with a spike connection because of the novel shape of insert member 80 carried in protrusion 76. Insert member 80, as shown, may be a block of plastic which may be smaller or flatter in its depth than its width or length, and defines a bore 82 passing generally diagonally through it as shown, so that the connecting spike will penetrate the bag wall at a position spaced from seal line 78.

Referring to FIG. 7, another flexible-walled protrusion 84 for a flexible, collapsible bag is disclosed. In this case, in a manner similar to FIG. 5, the two sides of the bag are folded along fold line 86 at the end of protrusion 84, and then sealed together by peripheral seal lines 88. Insert member 90, trapped within protrusion 84, may be roughly triangular in shape as shown, and defines a bore 92 extending therethrough. As shown, the area of insert member 90 adjacent one end 94 of the aperture is transversely enlarged relative to the area 96 of insert member 90 adjacent the other end. This triangular configuration facilitates the use of a more tightly fitting, generally triangular, flexible-walled protrusion.

Referring to FIGS. 8 to 10, another design of molded insert member 98 is disclosed, being capable of fitting in a flexible-walled collapsible bag of any desired design, either captured in a protrusion, or loosely in the bag, or adhered to the inner bag wall. Aperture or bore 100 is provided to receive a connecting spike penetrating through the bag wall, while various ribs 102, 104 are provided for ease of manually gripping the device through the bag wall.

Figure 11:
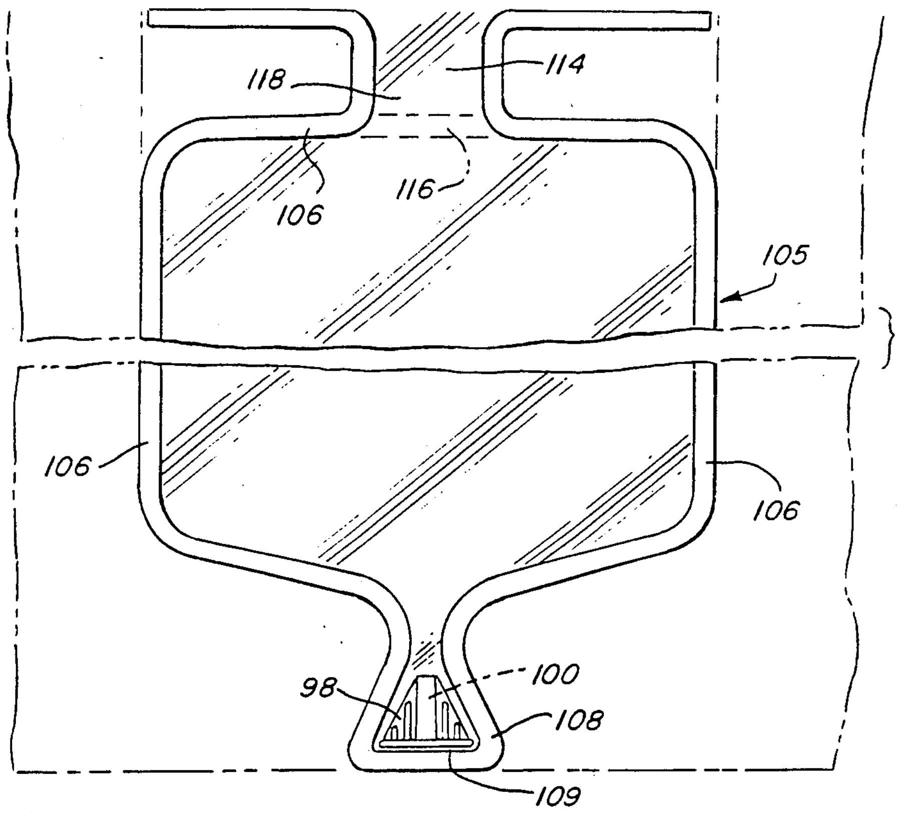
FIG. 11 is a plan view of another design of flexible collapsible container in accordance with this invention.
Figure 12:
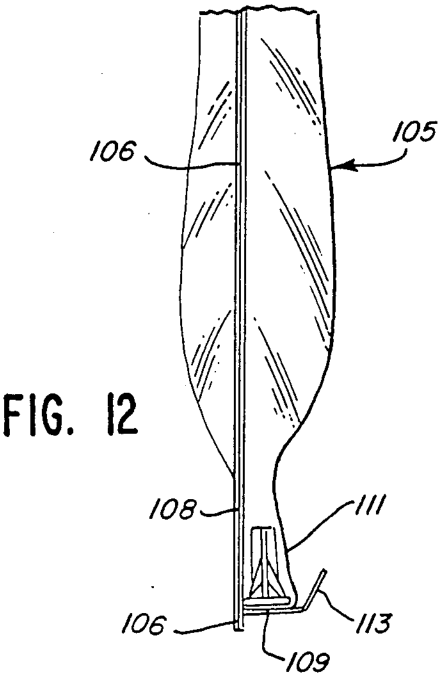
FIG. 12 is a fragmentary elevational view of the container of FIG. 11, rotated 90° about its longitudinal axis.

Referring to FIGS. 11 and 12, another design of container 105 is disclosed, comprising a pair of thermoplastic sheets lying one on top of the other and sealed together with a peripheral heat seal 106. Relatively narrow neck portion 108 is defined by part of heat seal 106 in a centered position on the container. Insert member 98, which may be of the design of FIGS. 8 to 10, is carried within neck portion 108 in a manner analogous to the previous embodiments, so that bore 100 extending through insert member 98 faces the end wall 109 of neck portion 108 to receive a puncture member in a manner similar to that previously described. Neck portion 108 may carry an offset portion 111 made by a thermoforming step or the like, so that a spike 34 can pass through end wall 109 without interference by peripheral heat seal 106.

Wall 109 may carry removable tape portion 113, if desired, similar in structure and function to tape member 30.

As delivered from the sealing machine, flexible container 105 may have an open end 114 to serve as a temporary filling port when bag 105 is delivered to a filling machine. Thereafter, a subsequent heat seal line 116 may be applied as shown to seal off the bag, and an appropriate hangar hole may be punched into the plastic material 118 outside of the seal lines 106, 116 for hanging of the container.

The flexible containers of this invention may be made by mass production techniques as described above, with significant cost savings over the puncturable, collapsible containers of the prior art. At the same time, they provide great convenience, reliability, and facility of use, particularly as containers for enteral feeding, blood or its components, or dialysis, parenteral, or washing solutions. They may be manufactured in a continuous form, fill and seal manufacturing process if desired.

The above has been offered for illustrative purposes only, and is not intended to limit the scope of the invention of this application, which is as defined in the claims below.

That which is claimed:

1. In a container comprising a flexible wall, and means for sealingly receiving a puncture member through said wall, which means comprises an insert member positioned within said container, said insert member defining an aperture with an end opening for sealingly receiving said puncture member after penetration through said wall, said aperture providing flow communication between the container interior and a puncture member received in said aperture, and means for securing said insert member in position to cause said aperture to have said end opening positioned adjacent a puncture member-penetrable portion of said flexible wall, said aperture having an axis that is generally perpendicular to said wall portion in said secured position.

2. The container of claim 1 in which said aperture is a bore extending through said insert member.

3. The container of claim 1 in which the container wall defines a flexible-walled protrusion communicating with the rest of the container through a relatively narrow neck portion, said insert member being retained in said protrusion.

4. The container of claim 3 in which said flexible-walled protrusion communicates from a corner of said container.

5. The container of claim 3 which is of generally diamond shape, said protrusion communicating with the rest of the container at one end thereof.

6. The container of claim 3 in which said protrusion defines an offset portion to facilitate access by a puncture member.

7. The container of claim 1 which carries removable tape means on said flexible wall, whereby said tape means may be removed to expose a clean surface for puncturing by said puncture member.

8. The container of claim 1 in which said insert member is a tubular member defining a pair of opposed, lateral projections to facilitate manual gripping of the insert member by the user.

9. The container of claim 1 in which said insert member defines an aperture which is a bore extending through said insert member, the area of said insert member adjacent one end of the bore being transversely enlarged relative to the area of the insert member adjacent the other end of said bore.

10. The container of claim 1 in which the wall material of said container adjacent said insert member is proportioned and of a type to permit the deforming of said wall material as a puncture member passes into said aperture to cause an annular portion of the container wall to deform into a position between the puncture member and the aperture wall, said annular portion being sealingly locked and seated between the connected puncture member and aperture wall to define a seal.

11. The method of manufacturing flexible, collapsible containers which comprises presenting to heat seal means a double layer web of theremoplastic material having opposed edges; sealing the double thickness web material together by said heat seal means to form generally diamond shaped containers in which a peripheral heat seal defines each diamond shaped container with at least two opposed lengths of said peripheral heat seal defining an acute angle to the opposed edges of said web, including the step of depositing between the two layers of the web an insert member defining a spike-receiving aperture, and forming a flexible-walled protrusion about said insert member which holds the insert member in a position whereby said spike-receiving aperture has an end opening positioned adjacent a puncture member-penetrable single thickness of said web material, said aperture having an axis that is generally perpendicular to said puncture member-penetrable portion to facilitate entry of a spike through said puncture member-penetrable portion into said aperture.

12. The method of claim 11 in which at least two lengths of said peripheral heat seal are generally parallel to the opposed edges of said web.

13. The method of claim 12 in which said peripheral heat seal forms at one end of said generally diamond shaped container a flexible-walled protrusion communicating with the remainder of said container.

14. The method of claim 13 in which, prior to said peripheral heat sealing, there is deposited between the two layers of said web an insert member defining a spike-receiving aperture, whereby the flexible-walled protrusion is formed by creation of said peripheral heat seal around the insert member.

15. The method of making a flexible collapsible container which comprises placing between a pair of overlapping, thermoplastic sheets an insert member which comprises an aperture for sealingly receiving a puncture member, in a position whereby said aperture has an end opening positioned adjacent a puncture member-penetrable portion of said flexible wall, said aperture having an axis that is generally perpendicular to said wall portion in said position, and therafter forming a peripheral seal line about said insert member to form said flexible, collapsible container from the pair of sheets which retains said insert member in said position.

16. The method of claim 15 in which said peripheral seal line defines a flexible-walled protrusion communicating with the rest of the container through a relatively narrow neck portion, said protrusion being formed about said insert member.

17. The method of claim 16 in which an offset portion is formed in said protrusion to facilitate access to the aperture by a puncture member passing through the container wall.

18. In a container comprising a flexible wall, and means for sealingly receiving a puncture member through said wall, which means comprises an insert member positioned within said container, said insert member defining an aperture having an end opening extending therethrough for sealingly receiving said puncture member after penetration through said wall, said aperture providing flow communication between the container interior and a puncture member received in said aperture, the container wall defining a flexible-wall protrusion communicating with the rest of the container through a relatively narrow neck portion, said insert member being retained in said protrusion in a position to cause said aperture to have an end opening positioned adjacent a puncture member-penetrable portion of said flexible wall, said aperture having an axis that is generally perpendicular to said wall portion in said secured position, the material of said wall portion being proportioned and of a type to permit the deforming of said material as a puncture member passes into said aperture, to cause an annular section of the container wall portion to deform into a position between the puncture member and the end opening, said annular portion being sealingly locked and seated between the connected puncture member and end opening to define a seal.

19. The container of claim 18 in which said flexible-walled protrusion communicates from a corner of said container.

20. The container of claim 18 which is of generally diamond shape, said protrusion communicating with the rest of the container at one end thereof.

21. The container of claim 18 in which said protrusion defines an offset portion to facilitate access by a puncture member.

22. The container of claim 21 in which said insert member is a tubular member defining a pair of opposed, lateral projections to facilitate manual gripping of the insert member by the user.

23. The container of claim 21 in which said insert member defines an area adjacent one end of said bore being transversely enlarged relative to the area of the insert member adjacent the other end of said bore.

* * * * *